United States Patent [19]

Nakao

[11] Patent Number: 5,847,174
[45] Date of Patent: Dec. 8, 1998

[54] METHOD FOR THE PREPARATION OF A POLYHALOGENO METAL COMPLEX COMPOUND

[75] Inventor: Yukimichi Nakao, Tsukuba, Japan

[73] Assignee: Agency of Industrial Science and Technology, Japan

[21] Appl. No.: 721,039

[22] Filed: Sep. 26, 1996

[30] Foreign Application Priority Data

Oct. 25, 1995  [JP]  Japan .................................. 7-277513

[51] Int. Cl.$^6$ .................................. C07F 1/00; C07F 3/00; C07F 5/00
[52] U.S. Cl. .................................. 556/1; 556/45; 556/64; 556/81; 556/110; 556/118; 556/138; 556/170
[58] Field of Search .................................. 556/1, 45, 64, 556/81, 110, 118, 138, 170

[56] References Cited

PUBLICATIONS

Chemical Abstracts, vol. 114, Abstract No. 197391, 1990.

*Primary Examiner*—Porfirio Nazario-Gonzalez
*Attorney, Agent, or Firm*—Wenderoth, Lind & Ponack

[57] ABSTRACT

Proposed is a method for the preparation of an ionic polyhalogeno metal complex compound consisting of a tetraalkylammonium cation and a polyhalogeno metal anion, of which the metal is selected from those having an atomic valency of 1 and a coordination number of 2, those having an atomic valency of 3 and a coordination number of 4 and those having an atomic valency of 2 and a coordination number of 4. The method comprises the steps of: dissolving a tetraalkylammonium halide and elementary halogen in a stoichiometric proportion corresponding to the chemical composition of the desired complex compound in an organic solvent to form a solution; dissolving, in the solution, the metal in an amount larger than the stoichiometric amount so as to be dissolved in the solution forming the complex compound in the reaction mixture; removing the undissolved metal from the reaction mixture to give a solution of the complex compound; and isolating the complex compound from the solution.

5 Claims, No Drawings

METHOD FOR THE PREPARATION OF A POLYHALOGENO METAL COMPLEX COMPOUND

BACKGROUND OF THE INVENTION

The present invention relates to a novel and efficient method for the preparation of a polyhalogeno metal complex compound or, more particularly, to an improved method by a single-step reaction for the preparation of a polyhalogeno metal complex compound consisting of a halogen metal anion and a tetraalkylammonium cation and having usefulness as a catalyst for various reactions and as an intermediate for the synthesis of other useful metal compounds.

In the prior art, there are known a variety of ionic polyhalogeno metal complex compounds or complex salts of a metal consisting of an ion pair of a cation and a polyhalogeno metal anion which is a combination of a metal cation and a plurality of halogen anions. These ionic polyhalogeno metal complex compounds are utilized as a catalyst for promoting various reactions and as an intermediate for the synthesis of other useful complex compounds.

These polyhalogeno metal complex compounds are prepared in the prior art from a metal halide as the starting material, which is obtained by dissolving a metal in the elementary form in an acid such as aqua regia, hydrochloric acid, hydrobromic acid, hydroiodic acid and the like as is described, for example, in Journal of Chemical Society, Dalton, 1973, page 1845. This prior art method, however, involves several problems and disadvantages as an industrial process because of the strong hygroscopicity or deliquescence of the metal halide compounds to cause a difficulty in handling thereof and troublesomeness of the process as a consequence of the plural number of steps involved therein if not to mention the relatively low yield of the desired product. When a polyhalogeno gold(I) complex compound is desired, for example, a traditional method therefor is first to prepare a gold(III) complex compound corresponding to the desired product followed by reduction of the gold(III) complex compound with hydrazine, acetone and the like as a reducing agent.

On the other hand, Japanese Patent Kokai 4-21726 teaches that various kinds of metals can be readily dissolved in a liquid medium which is a solution of an elementary halogen and a soluble halogen compound in a solvent selected from water and polar organic solvents. Japanese Patent Kokai 4-6229 also teaches that various kinds of metals can be readily dissolved in a liquid medium which is a solution of a cationic surface active agent having a halogen ion as the counter anion and an elementary halogen in an organic solvent. It is suggested in these references that the metal is dissolved in the solvent by forming a polyhalogeno metal-anionic complex compound having high solubility. It is not clear from these disclosures, however, in what conditions such an ionic polyhalogeno metal complex compound can be obtained in a high efficiency.

SUMMARY OF THE INVENTION

The present invention accordingly has an object to provide a novel method for the preparation of an ionic polyhalogeno metal complex compound having usefulness as a catalyst for various reactions or as an intermediate for the preparation of other useful metal complex compounds from a metal in the elementary form by a single step reaction.

Thus, the method of the present invention for the preparation of an ionic polyhalogeno metal complex compound consisting of a polyhalogeno metal anion and a tetraalkylammonium cation comprises the steps of:

(a) dissolving a halogen, which is the halogen forming the polyhalogeno metal anion, in the elementary form and a tetraalkylammonium halide, which is a halide of the tetraalkylammonium cation, in an organic solvent to form a solution;

(b) adding, to the solution, a metal, which is the metal forming the polyhalogeno metal anion, in such an amount as to leave an undissolved portion of the metal after establishment of constancy in the dissolved amount of the metal in the reaction mixture;

(c) removing the undissolved portion of the metal from the reaction mixture to give a solution containing the ionic polyhalogeno metal complex compound; and (d) removing the organic solvent from the solution obtained in step (c).

DETAILED DESCRIPTION OF THE PREFERRED EMBODIMENTS

As is understood from the above given summarizing description, the inventive method for the preparation of an ionic polyhalogeno metal complex compound involves a single reaction so that the desired product can be obtained very efficiently and economically.

The ionic polyhalogeno metal complex compound obtained as the product of the above defined inventive method is represented by the general formula

  (I)

  (II)

  (III)

or

  (IV)

in which R is, each independently from the others, an alkyl group having 1 to 30 carbon atoms, X is an atom of a halogen such as chlorine, bromine and iodine, $M^I$ is an atom of a metal having a coordination number of 2 and an atomic valency of 1, $M^{II}$ is an atom of a metal having a coordination number of 4 and an atomic valency of 2 and $M^{III}$ is an atom of a metal having a coordination number of 4 and an atomic valency of 3.

The reactions leading to the formation of these ionic polyhalogeno metal complex compounds of the general formulas (I) to (IV) can be expressed by the following reaction equations:

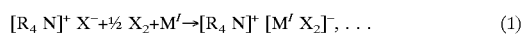  (1)

  (2)

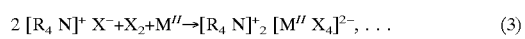  (3)

and

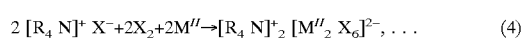  (4)

respectively, in which each symbol has the same meaning as defined above.

The alkyl group denoted by R having 1 to 30 carbon atoms, which can be straightly linear, branched or cyclic, is exemplified by methyl, ethyl, propyl, butyl, hexyl, octyl, decyl, dodecyl, pentadecyl, hexadecyl, octadecyl, cyclopentyl, and cyclohexyl group without particular limitations although the inventive method is most successfully applicable to the cases in which at least three of the four R groups are lower alkyl groups having 1 to 4 carbon atoms. The halogen denoted by X includes chlorine, bromine and iodine. The metals denoted by $M^I$, $M^{II}$ and $M^{III}$, to which the inventive method is applicable, include silver, gold and mercury as the examples of $M^I$, beryllium, magnesium, tin, iron, lead, cobalt, nickel, palladium, platinum, zinc, mercury and manganese as the examples of $M^{II}$ and aluminum, indium, antimony, bismuth, iron, gold and chromium as the examples of $M^{III}$.

In step (a) of the inventive method, a halogen in the elementary form and a tetraalkylammonium halide are dissolved in an organic solvent to give a solution as a reaction medium. The organic solvent is not particularly limitative provided that the solutes can be readily dissolved therein and the solvent is inert to these solutes. Examples of suitable organic solvents include alcohols, ketones, nitriles and hydrocarbons such as methyl alcohol, ethyl alcohol, acetone, acetonitrile, benzene and the like. These organic solvents can be used either singly or as a mixture of two kinds or more according to need.

Examples of the tetraalkylammonium halide represented by the general formula $[R_4 N]^+ X^-$, in which R and X each have the same meaning as defined above, include tetraethylammonium chloride, tetraethylammonium bromide, tetraethylammonium iodide, tetrabutylammonium chloride, tetrabutylammonium bromide, tetrabutylammonium iodide, trimethylstearylammonium chloride, trimethylstearylammonium bromide and trimethylstearylammonium iodide.

It is important in the preparation of the solution as the reaction medium by dissolving a halogen and a tetraalkylammonium halide in an organic solvent that the proportion of these solutes dissolved in the solvent is stoichiometric as closely as possible according to either one of the above given reaction equations (1) to (4) depending on the types of the metal in order that the polyhalogeno metal complex compound obtained by the inventive method has a chemical composition expressed by either one of the formulas (I) to (IV) in a purity as high as possible.

In step (b) of the inventive method, the thus prepared solution as the reaction medium is admixed with a metal according to desire, preferably, in the form of a fine wire or fine particles so that the metal is readily dissolved in the solution by the reaction according to the reaction equations (1) to (4). The reaction can be promoted by increasing the temperature so that the reaction mixture containing the elementary metal is heated under reflux of the organic solvent.

The amount of the metal added to the reaction medium in step (b) of the inventive method should be in excess over the stoichiometric amount defined by either one of the reaction equations (1) to (4) according to the type of the desired product so that the free halogen and the tetraalkylammonium halide contained in the reaction medium are substantially completely consumed by the reaction with the metal leaving an undissolved portion of the metal. Namely, the undissolved portion of the metal is periodically taken out of the reaction mixture to monitor the progress of the reaction and, when the amount of the undissolved portion of the metal is not decreased by further continuing the reaction, the reaction can be assumed to be completed. The reaction time required for completion of the reaction naturally depends on various factors such as the types of the starting reactants and the proportion thereof, concentration of the reactants in the reaction medium, reaction temperature and so on but the reaction is complete in many cases within 0.5 to 150 hours.

In step (c) of the inventive method after completion of the reaction in step (b), the undissolved or unreacted portion of the metal is taken out of the reaction mixture to give a solution containing the desired complex compound dissolved therein. When this solution is chilled as such or after concentration to have an appropriately increased concentration of the complex compound, the complex compound as the desired product is precipitated out in a crystalline form. Alternatively, the solution is freed from the organic solvent by distillation and the solid residue is dissolved in and recrystallized from a suitable organic solvent.

Examples of the ionic polyhalogeno metal complex compounds consisting of a polyhalogeno metal anion and a tetraalkylammonium cation which can be prepared by the inventive method include those expressed by the formulas: $[(C_2 H_5)_4 N]^+ [AuCl_4]^-$, $[(C_2 H_5)_4 N]^+ [AuBr_4]^-$, $[(C_4 H_9)_4 N]^+ [AuBr_2]^-$, $[C_{18} H_{37} (CH_3)_3 N]^+ [AuI_2]^-$, $[(C_2 H_5)_4 N]^+_2 [Pd_2 I_6]^{2-}$, $[(C_4 H_9)_4 N]^+ [AgBr_2]^-$ and $[(C_4 H_9)_4 N]^+_2 [ZnBr_4]^{2-}$ although many other similar complex compounds can be prepared according to the inventive method.

In the following, the method of the present invention is described in more detail by way of examples, which, however, never limit the scope of the invention in any way.

EXAMPLE 1

A solution as a reaction medium was prepared by dissolving 106.5 mg (1.5 mmoles) of chlorine and 165.5 mg (1.0 mmole) of tetraethylammonium chloride in 10 g of acetonitrile. A gold wire having a diameter of 0.2 mm and weighing 236 mg (1.2 mmoles) was added to the solution which was agitated and heated under reflux of the solvent so that the gold wire was gradually dissolved in the solution. After 2 hours of heating of the reaction mixture, the dissolved amount of the gold wire reached 200.5 mg (1.018 mmoles) and was no longer increased by further continuing the reaction as was evidenced by the periodical measurements of the weight of the undissolved wire residue.

The reaction mixture was, after removal of the undissolved gold wire residue, freed from the solvent under reduced pressure to dryness and the solid residue was redissolved in 70 ml of ethyl alcohol and recrystallized therefrom followed by filtration and drying of the precipitates to give 414 mg of a yellow crystalline product which was a gold(III) complex compound having a chemical composition expressed by the formula $[(C_2 H_5)_4 N]^+ [AuCl_4]^-$ as was indicated by the results of the elementary analysis. The above mentioned yield of the complex compound was 86.7% of the theoretical value based on the dissolved amount of the metal wire as calculated from the assumed reaction equation given below:

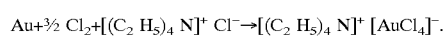

$$Au + \tfrac{3}{2} Cl_2 + [(C_2 H_5)_4 N]^+ Cl^- \rightarrow [(C_2 H_5)_4 N]^+ [AuCl_4]^-.$$

EXAMPLE 2

A solution as a reaction medium was prepared by dissolving 240 mg (1.5 mmoles) of bromine and 210 mg (1.0 mmole) of tetraethylammonium bromide in 10 g of acetonitrile. A gold wire having a diameter of 0.2 mm and weighing 236 mg (1.2 mmoles) was added to the solution which was agitated and heated under reflux of the solvent so that the gold wire was gradually dissolved in the solution. After 2 hours of heating of the reaction mixture, the dissolved amount of the gold wire reached 197.2 mg (1.001 mmoles) and was no longer increased by further continuing the reaction as was evidenced by the periodical measurements of the weight of the undissolved wire residue.

The reaction mixture was, after removal of the undissolved gold wire residue, freed from the solvent under reduced pressure to dryness and the solid residue was redissolved in 120 ml of ethyl alcohol and recrystallized therefrom followed by filtration and drying of the precipitates to give 548 mg of a dark red crystalline product which was a gold(III) complex compound having a chemical composition expressed by the formula $[(C_2H_5)_4N]^+[AuBr_4]^-$ as was indicated by the results of the elementary analysis. The above mentioned yield of the complex compound was 84.6% of the theoretical value as calculated from the assumed reaction equation given below:

$$Au + \tfrac{3}{2} Br_2 + [(C_2H_5)_4N]^+ Br^- \rightarrow [(C_2H_5)_4N]^+ [AuBr_4]^-.$$

EXAMPLE 3

A solution as a reaction medium was prepared by dissolving 80 mg (0.5 mmole) of bromine and 322 mg (1.0 mmole) of tetrabutylammonium bromide in 10 g of acetonitrile. A gold wire having a diameter of 0.2 mm and weighing 236 mg (1.2 mmoles) was added to the solution which was agitated and heated under reflux of the solvent so that the gold wire was gradually dissolved in the solution. After 96 hours of heating of the reaction mixture, the dissolved amount of the gold wire reached 166.7 mg (0.847 mmole) and was no longer increased by continuing the reaction as was evidenced by the periodical measurements of the weight of the undissolved wire residue.

The reaction mixture was, after removal of the undissolved gold wire residue, freed from the solvent under reduced pressure to dryness and the solid residue was redissolved in a mixture of 2 ml of ethyl alcohol and 0.2 ml of acetone and recrystallized therefrom followed by filtration and drying of the precipitates to give 364 mg of an orange-colored crystalline product which was a gold(I) complex compound having a chemical composition expressed by the formula $[(C_4H_9)_4N]^+[AuBr_2]^-$ as was indicated by the results of the elementary analysis. The above mentioned yield of the complex compound was 78.7% of the theoretical value as calculated from the assumed reaction equation given below:

$$Au + \tfrac{1}{2} Br_2 + [(C_4H_9)_4N]^+ Br^- \rightarrow [(C_4H_9)_4N]^+ [AuBr_2]^-.$$

EXAMPLE 4

A solution as a reaction medium was prepared by dissolving 127 mg (0.5 mmole) of iodine and 439 mg (1.0 mmole) of trimethylstearylammonium iodide in 10 g of benzene. A gold wire having a diameter of 0.2 mm and weighing 236 mg (1.2 mmoles) was added to the solution which was agitated and heated under reflux of the solvent so that the gold wire was gradually dissolved in the solution. After 24 hours of heating of the reaction mixture, the dissolved amount of the gold wire reached 188.9 mg (0.959 mmole) and was no longer increased by further continuing the reaction as was evidenced by the periodical measurements of the weight of the undissolved wire residue.

The reaction mixture was, after removal of the undissolved gold wire residue, chilled at 5° C. and the crystalline precipitates formed therein were collected by filtration and dried to give 610 mg of a yellowish orange crystalline product which was a gold(I) complex compound having a chemical composition expressed by the formula $[C_{18}H_{37}(CH_3)_3N]^+[AuI_2]^-$ as was indicated by the results of the elementary analysis. The above mentioned yield of the complex compound was 83.3% of the theoretical value as calculated from the assumed reaction equation given below:

$$Au + \tfrac{1}{2} I_2 + [C_{18}H_{37}(CH_3)_3N]^+ I^- \rightarrow [C_{18}H_{37}(CH_3)_3N]^+ [AuI_2]^-.$$

EXAMPLE 5

A solution as a reaction medium was prepared by dissolving 254 mg (1.0 mmole) of iodine and 257 mg (1.0 mmole) of tetraethylammonium iodide in 10 g of acetonitrile. A palladium wire having a diameter of 0.2 mm and weighing 127.7 mg (1.2 mmoles) was added to the solution which was agitated and heated under reflux of the solvent so that the palladium wire was gradually dissolved in the solution. After 4 hours of heating of the reaction mixture, the dissolved amount of the palladium wire reached 106.8 mg (1.004 mmoles) and was no longer increased by further continuing the reaction as was evidenced by the periodical measurements of the weight of the undissolved wire residue.

The reaction mixture was, after removal of the undissolved palladium wire residue, chilled at 5° C. and the crystalline precipitates formed therein were collected by filtration and dried to give 532 mg of a black crystalline product which was a palladium(II) complex compound having a chemical composition expressed by the formula $[(C_2H_5)_4N]^+_2[Pd_2I_6]^{2-}$ as was indicated by the results of the elementary analysis. The above mentioned yield of the complex compound was 85.8% of the theoretical value as calculated from the assumed reaction equation given below:

$$2Pd + 2I_2 + 2[(C_2H_5)_4N]^+ I^- \rightarrow [(C_2H_5)_4N]^+_2 [Pd_2I_6]^{2-}.$$

EXAMPLE 6

A solution as a reaction medium was prepared by dissolving 80 mg (0.5 mmole) of bromine and 322 mg (1.0 mmole) of tetrabutylammonium bromide in 10 g of acetonitrile. A silver wire having a diameter of 0.2 mm and weighing 129.5 mg (1.2 mmoles) was added to the solution which was agitated and heated under reflux of the solvent so that the silver wire was gradually dissolved in the solution. After 2 hours of heating of the reaction mixture, the dissolved amount of the silver wire reached 86.5 mg (0.802 mmole) and was no longer increased by further continuing the reaction as was evidenced by the periodical measurements of the weight of the undissolved wire residue.

The reaction mixture was, after removal of the undissolved silver wire residue, freed from the solvent under reduced pressure to dryness and the solid residue was redissolved in a mixture of 15 ml of methyl isobutyl ketone and 10 ml of cyclohexane and recrystallized therefrom followed by filtration and drying of the precipitates to give 216 mg of a white crystalline product which was a silver(I) complex compound having a chemical composition expressed by the formula $[(C_4H_9)_4N]^+[AgBr_2]^-$ as was indicated by the results of the elementary analysis. The above mentioned yield of the complex compound was 52.8% of the theoretical value as calculated from the assumed reaction equation given below:

$$Ag + \tfrac{1}{2} Br_2 + [(C_4H_9)_4N]^+ Br^- \rightarrow [(C_4H_9)_4N]^+ [AgBr_2]^-.$$

EXAMPLE 7

A solution as a reaction medium was prepared by dissolving 80 mg (0.5 mmole) of bromine and 322 mg (1.0 mmole) of tetrabutylammonium bromide in 10 g of acetonitrile. A zinc wire having a diameter of 0.2 mm and weighing 78.5 mg (1.2 mmoles) was added to the solution which was agitated and heated under reflux of the solvent so that the zinc wire was gradually dissolved in the solution. After 1 hour of heating of the reaction mixture, the dissolved amount of the zinc wire reached 33.3 mg (0.509 mmole) and was no longer increased by further continuing the reaction as was evidenced by the periodical measurements of the weight of the undissolved wire residue.

The reaction mixture was, after removal of the undissolved zinc wire residue, freed from the solvent under reduced pressure to dryness and the solid residue was redissolved in 40 ml of ethyl alcohol and recrystallized therefrom followed by filtration and drying of the precipitates to give 121 mg of a white crystalline product which was a zinc(II) complex compound having a chemical composition expressed by the formula $[(C_4 H_9)_4 N]^+_2 [ZnBr_4]^{2-}$ as was indicated by the results of the elementary analysis. The above mentioned yield of the complex compound was 78.7% of the theoretical value as calculated from the assumed reaction equation given below:

$$\tfrac{1}{2} Zn + \tfrac{1}{2} Br_2 + [(C_4 H_9)_4 N]^+ Br^- \rightarrow \tfrac{1}{2} [(C_4 H_9)_4 N]^+_2 [ZnBr_4]^{2-}.$$

What is claimed is:

1. A method for the preparation of an ionic polyhalogeno metal complex compound which comprises the steps of:
   (a) dissolving a halogen, which is the halogen forming the polyhalogeno metal anion, in the elementary form and a tetraalkylammonium halide, which is a halide of the tetraalkylammonium cation, in an organic solvent to form a solution;
   (b) adding, to the solution, a metal, which is the metal forming the polyhalogeno metal anion, in such an amount as to leave an undissolved portion of the metal after establishment of constancy in the dissolved amount of the metal in the solution as a reaction mixture;
   (c) removing the undissolved portion of the metal from the reaction mixture to give a solution containing the ionic polyhalogeno metal complex compound; and
   (d) removing the organic solvent from the solution obtained in step (c).

2. A method for the preparation of an ionic polyhalogeno metal complex compound represented by the general formula $$[R_4 N]^+ [M^I X_2]^-,$$

in which each R is, independently from the others, an alkyl group, $M^I$ is an atom of a metal having an atomic valency of 1 and a coordination number of 2 and X is an atom of a halogen, which comprises the steps of:
   (a) dissolving, in an organic solvent, a tetraalkylammonium halide $[R_4 N]^+ X^-$ and elementary halogen $X_2$ in substantially equimolar amounts calculated as the halogen atoms to form a solution;
   (b) adding, to the solution, an elementary form of the metal $M^I$ in an at least equimolar amount to the tetraalkylammonium halide to be dissolved in the solution forming an ionic complex compound in the reaction mixture;
   (c) removing the undissolved portion of the metal from the reaction mixture to give a solution of the ionic polyhalogeno metal complex compound; and
   (d) removing the organic solvent from the solution obtained in step (c).

3. A method for the preparation of an ionic polyhalogeno metal complex compound represented by the general formula $$[R_4 N]^+ [M^{III} X_4]^-,$$

in which each R is, independently from the others, an alkyl group, $M^{III}$ is an atom of a metal having an atomic valency of 3 and a coordination number of 4 and X is an atom of a halogen, which comprises the steps of:
   (a) dissolving, in an organic solvent, a tetraalkylammonium halide $[R_4 N]^+ X^-$ and elementary halogen $X_2$ in a molar proportion substantially equal to 1:3 calculated as the halogen atoms to form a solution;
   (b) adding, to the solution, an elementary form of the metal $M^{III}$ in an at least equimolar amount to the tetraalkylammonium halide to be dissolved in the solution forming an ionic complex compound in the reaction mixture;
   (c) removing the undissolved portion of the metal from the reaction mixture to give a solution of the ionic polyhalogeno metal complex compound; and
   (d) removing the organic solvent from the solution obtained in step (c).

4. A method for the preparation of an ionic polyhalogeno metal complex compound represented by the general formula $$[R_4 N]^+_2 [M^{II} X_4]^{2-},$$

in which each R is, independently from the others, an alkyl group, $M^{II}$ is an atom of a metal having an atomic valency of 2 and a coordination number of 4 and X is an atom of a halogen, which comprises the steps of:
   (a) dissolving, in an organic solvent, a tetraalkylammonium halide $[R_4 N]^+ X^-$ and elementary halogen $X_2$ in substantially equimolar amounts calculated as the halogen atoms to form a solution;
   (b) adding, to the solution, an elementary form of the metal $M^{II}$ in an amount of at least 0.5 mole per mole of the tetraalkylammonium halide to be dissolved in the solution forming an ionic complex compound in the reaction mixture;
   (c) removing the undissolved portion of the metal from the reaction mixture to give a solution of the ionic polyhalogeno metal complex compound; and
   (d) removing the organic solvent from the solution obtained in step (c).

5. A method for the preparation of an ionic polyhalogeno metal complex compound represented by the general formula $$[R_4 N]^+_2 [M^{II}_2 X_6]^{2-},$$

in which each R is, independently from the others, an alkyl group, $M^{II}$ is an atom of a metal having an atomic valency of 2 and a coordination number of 4 and X is an atom of a halogen, which comprises the steps of:
   (a) dissolving, in an organic solvent, a tetraalkylammonium halide $[R_4 N]^+ X^-$ and elementary halogen $X_2$ in a molar proportion substantially equal to 1:2 calculated as the halogen atoms to form a solution;
   (b) adding, to the solution, an elementary form of the metal $M^{II}$ in an at least equimolar amount to the tetraalkylammonium halide to be dissolved in the solution forming an ionic complex compound in the reaction mixture;
   (c) removing the undissolved portion of the metal from the reaction mixture to give a solution of the ionic polyhalogeno metal complex compound; and
   (d) removing the organic solvent from the solution obtained in step (c).

* * * * *